United States Patent [19]

Gillies et al.

[11] Patent Number: 5,036,464
[45] Date of Patent: Jul. 30, 1991

[54] METHODS OF DETECTING ENDOSCOPE INSERTION DIRECTION

[75] Inventors: Duncan F. Gillies, London, England; Gul N. Khan, Islamabad, Pakistan; Yutaka Takahashi, Hachioji, Japan

[73] Assignee: Olympus Optical Co., Ltd., Tokyo, Japan

[21] Appl. No.: 523,506

[22] Filed: May 15, 1990

[30] Foreign Application Priority Data

Nov. 24, 1989 [GB] United Kingdom ............... 8926542

[51] Int. Cl.$^5$ ............................................. G06F 15/42
[52] U.S. Cl. ............................ 364/413.13; 364/413.15; 364/413.22; 358/98; 128/6
[58] Field of Search ................. 364/413.13, 413.15, 364/413.22; 358/98; 128/6

[56] References Cited

U.S. PATENT DOCUMENTS

| 4,834,070 | 5/9189 | Saitou .................................. 128/6 |
| 4,891,696 | 1/1990 | Miyazaki ............................ 358/98 |
| 4,910,590 | 3/1990 | Gillies et al. ...................... 358/98 |
| 4,916,533 | 4/1990 | Gillies et al. ...................... 358/98 |
| 4,959,710 | 9/1990 | Uehara et al. .................... 358/98 |

Primary Examiner—Jerry Smith
Assistant Examiner—Russell E. Cass
Attorney, Agent, or Firm—Armstrong, Nikaido, Marmelstein, Kubovcik & Murray

[57] ABSTRACT

The method of detecting the direction of insertion of an endoscope includes the steps of a) forming a system of images made of a plurality of picture images which have a different number of pixels from the same endoscope image, and b) extracting a spatially largest region including an average gray level and variance of gray level within predetermined ranges by examining the average gray level and variance of the gray level of respective pixels in a plurality of picture images formed by the forming step. The region extracted by the extracting step is considered to be an endoscope insertion direction.

10 Claims, 9 Drawing Sheets

METHODS OF DETECTING ENDOSCOPE INSERTION DIRECTION

BACKGROUND OF THE INVENTION

1. Field of the Invention

This invention relates to methods of detecting the direction of insertion of an endoscope, particularly to methods adapted to facilitate the insertion direction of an endoscope in the inspection field of a large intestine, possibly by automatic control.

2. Related Art Statement

Recently, there has been increasing use of endoscopes to enable organs within a body cavity to be observed by inserting an elongated insertion sheath. Various therapies can be applied by using medical tools inserted through a channel in the sheath as required.

In a conventional endoscope inspection, a doctor determines the advancing direction of the endoscope (insertion sheath) by observing the endoscope image.

However, a high degree of technical skill is required to insert an endoscope when inspecting the large intestine.

The applicants have proposed a method of detecting an endoscope insertion direction in which a dark region is extracted in an endoscope image and is considered an endoscope insertion direction in U.S. Pat. No. 4,910,590. In the method described in this patent, first of all, a quadtree with respect to the brightness level (gray level) is constructed by the steps shown in FIG. 9 of the patent mentioned above. That is, where the total pixels of the original picture number $n \times n$, the average gray level of the region of $2 \times 2$ pixels is obtained and the quadtree is constructed by repeating the operations for obtaining an image of pixels of $n/2 \times n/2$ until the number of pixels becomes one. Thus, after the quadtree with respect to the gray level is constructed, a dark region is extracted by the steps shown in FIG. 14 of the patent mentioned above. That is to say, operations are carried out as follows. A node of the closest value to the required gray level is extracted in the order from the upper plane of the quadtree and then a node of the closest value to the required gray level is extracted from among four child nodes of this extracted node. Then, where the extracted node is included in a predetermined plane and also included within a predetermined range of the required gray level, it is examined whether the difference of the gray levels of four child nodes of the extracted node is included within a constant value or not. In the case where it is included within a constant value, the node is defined as the required dark region. On the other hand, where the difference of the gray level of four child nodes is not included within a constant value and also corresponds to the bottom plane which may be completed, "back-track" is carried out. This "back-track" is to return to the plane of an upper level and to examine the remaining three child nodes which belong to the same parent node as the extracted node.

Thus, in the method described in the patent mentioned above, when the dark region is extracted, erroneously determining the dark region, caused by a broken light fiber which forms an image guide of an endoscope, noise and others, to be the insertion direction, is prevented.

However, in some endoscope images, processing time becomes long by repeating the above mentioned back tracks several times, so that there is more room for improvement.

OBJECT AND SUMMARY OF THE INVENTION

It is an object of the present invention to provide a method of detecting the insertion direction of an endoscope whereby the insertion direction can be detected within a short processing time.

Another object of the invention is to provide a method of detecting the insertion direction of an endoscope whereby the insertion direction can be accurately detected.

The method of detecting the insertion direction of an endoscope of the present invention comprises the steps of: forming a system of images made from a plurality of images which have different number of pixels from the same endoscope image; and extracting the spatially largest region in which an average gray level and variance of gray level are included within predetermined ranges by examining the average gray level and variance of the gray level of respective pixels in a plurality of picture images formed by the forming step mentioned above. The region extracted by the extracting step mentioned above is considered the insertion direction of an endoscope.

BRIEF DESCRIPTION OF THE DRAWINGS

FIG. 1 is an explanatory view showing an endoscope inserted in the large intestine.

FIG. 2 is a perspective view showing a tip of an endoscope insertion sheath.

FIG. 3 is an explanatory view showing the tip of an endoscope inserted in a bent part of the large intestine.

FIG. 4 is an explanatory view showing an endoscope image which would be seen with the endoscope as shown in FIG. 3.

FIG. 5 is an explanatory view showing the tip of an endoscope inserted in a straight part of the large intestine.

FIG. 6 is an explanatory view showing an endoscope image which would be seen with the endoscope as shown in FIG. 5.

FIG. 7 is an explanatory view showing an example of an endoscope apparatus using a fiberscope and externally fitted television camera.

FIG. 8 is an explanatory view showing an example of an endoscope apparatus using a videoscope.

FIG. 9 is a flow chart showing a method of the embodiments of the present invention.

FIG. 10 is a typical histogram with respect to a gray level of an endoscope image.

FIG. 11 is an explanatory view showing a pyramid based on a quadtree.

FIG. 12 is a flow chart showing operations (2 - a) in step 2.

FIG. 13 is a flow chart showing operations (2 - b) in step 2.

FIG. 14 is an explanatory view of u-link.

DETAILED DESCRIPTION OF THE PREFERRED EMBODIMENTS

First of all, a summary of the present invention will be given by the explanation With reference to FIGS. 1 to 6.

Figure 1:
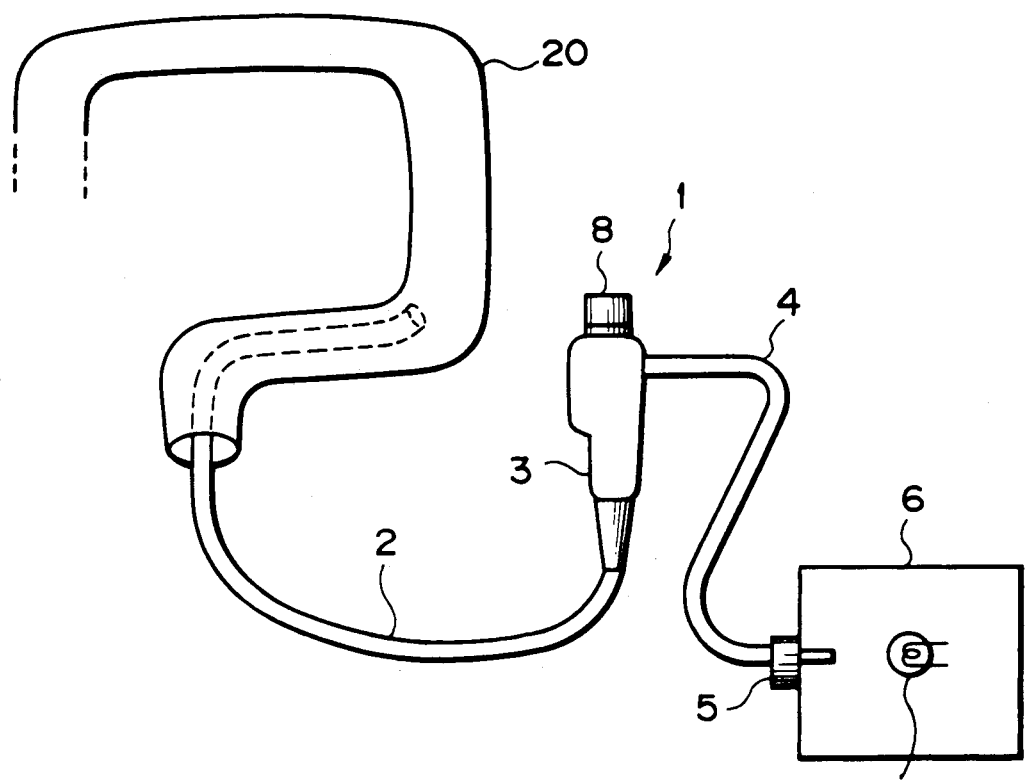
FIGS. 1 to 14 relate to an embodiment of the present invention.

As shown in FIG. 1, an endoscope (fiberscope) 1 is provided with an elongated flexible insertion sheath 2 and an operating part 3 with a thick diameter connected to the rear end of the insertion sheath 2. A flexible cord (universal cord) 4 is extended sidewise from the operating part 3, and is provided at its tip with a connector 5, which can be connected to a light source apparatus 6. The operating part 3 is provided at its rear end with an eyepiece part 8.

Figure 2:
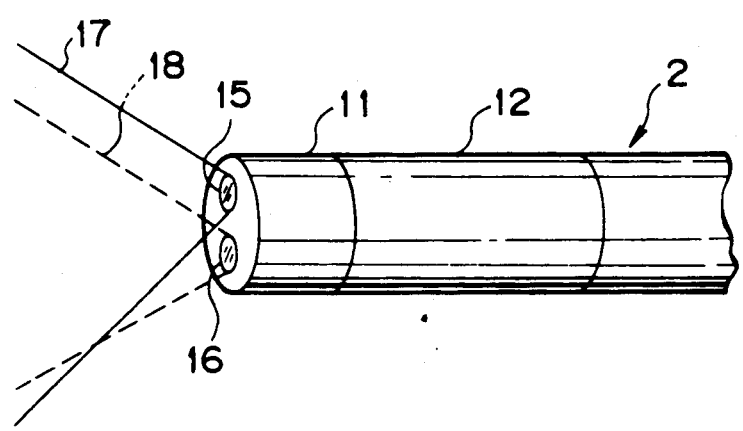

As shown in FIG. 2, a rigid tip part 11 and a rearward curvable part 12 adjacent to this tip part 11 are successively provided at the tip of the insertion sheath 2. A curving operation knob (not illustrated) is provided on the operating part 3. The above mentioned curvable part 12 can be curved vertically and/or horizontally by turning and operating this curving operation knob.

An illuminating lens 15 of an illuminating optical system and an objective lens 16 of an observing optical system are arranged in the rigid tip part 11 and are directed substantially in the same direction as the tip part 11. A light guide (not illustrated), made of, for example, a fiber bundle is provided at the rear end of the illuminating lens 15. This light guide is inserted through the insertion sheath 2, operating part 3 and universal cord 4, and is connected to the connector 5. When this connector 5 is connected to the above mentioned light source apparatus 6, the illuminating light emitted by a lamp 6a within this light source apparatus 6 will enter the incident end of the light guide. The illuminating light will be led to the tip part 11 by the above mentioned light guide and will be emitted by the tip end face to be radiated out to an object through the illuminating lens 15. In FIG. 2, the reference numeral 17 represents an illuminated region of the illuminating light.

On the other hand, the tip end face of an image guide (not illustrated), made of, for example, a fiber bundle (not illustrated) is arranged in the image forming position of the above mentioned objective lens 16. This image guide is inserted through the insertion sheath 2 and extended to the eyepiece part 8. The object image formed by the objective lens 16 will be led to the eyepiece part 8 and will be observed through an eyepiece lens (not illustrated). In FIG. 2, the reference numeral 18 represents a visual field of the observing optical system.

As shown in FIG. 2, the illuminating optical system and observing optical system of the endoscope 1 are adjacent to each other and are directed substantially in the same direction. Accordingly, it can be said that the dark region of an endoscope image is the farthest from the tip. Therefore, as shown in FIG. 1, in case the endoscope 1 (insertion sheath 2) is inserted into a closed tube such as a large intestine 20, the endoscope 1 can be inserted in the direction of the darkest region of the obtained endoscope image. This will be explained with reference to FIGS. 3 to 6. FIGS. 4 and 6 show parts of equal brightness by means of shading. The regions represented by the reference numerals 21, 22 and 23 show parts in increasing order of brightness.

Figure 3:
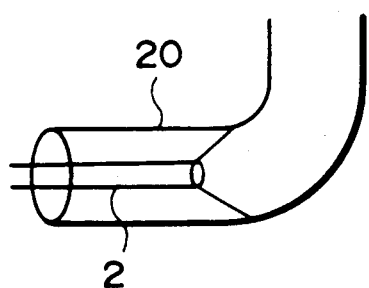
Figure 4:
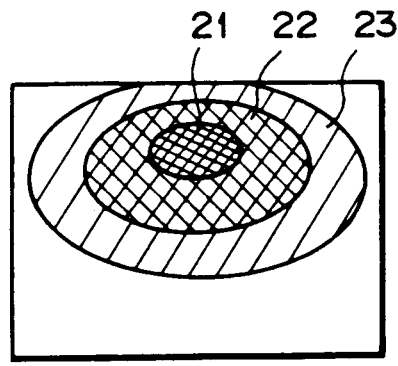

FIG. 3 shows the insertion sheath 2 of the endoscope 1 inserted into an upward bend of the large intestine 20. In this case, as shown in FIG. 4, the dark region in the endoscope image appears at the top of the image. Therefore, in this case, the tip part of the endoscope 1 can be curved upward and the insertion sheath 2 can be inserted upward.

Figure 5:
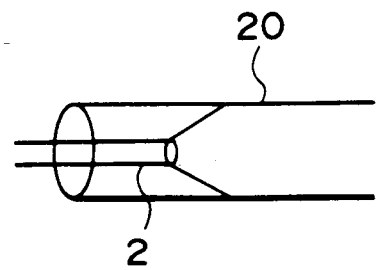
Figure 6:
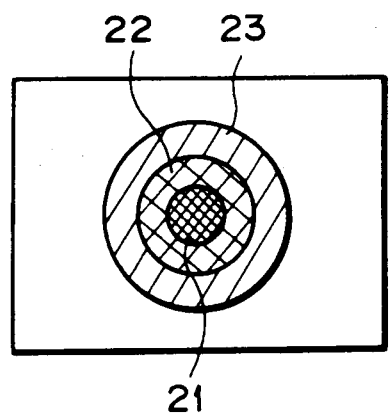

FIG. 5 shows the insertion sheath 2 of the endoscope 1 inserted in a straight part of the large intestine 20. In this case, as shown in FIG. 6, the dark region in the endoscope image appears in the center. Therefore, in this case, the insertion sheath 2 of the endoscope 1 can be inserted straight as it is.

Thus, the method of detecting the insertion direction of an endoscope of the present invention is to detect the endoscope insertion direction by extracting a dark region of an endoscope image and is further to accurately extract the dark region of the endoscope image.

An embodiment of the present invention will be explained with reference to FIGS. 7 to 14.

Figure 7:
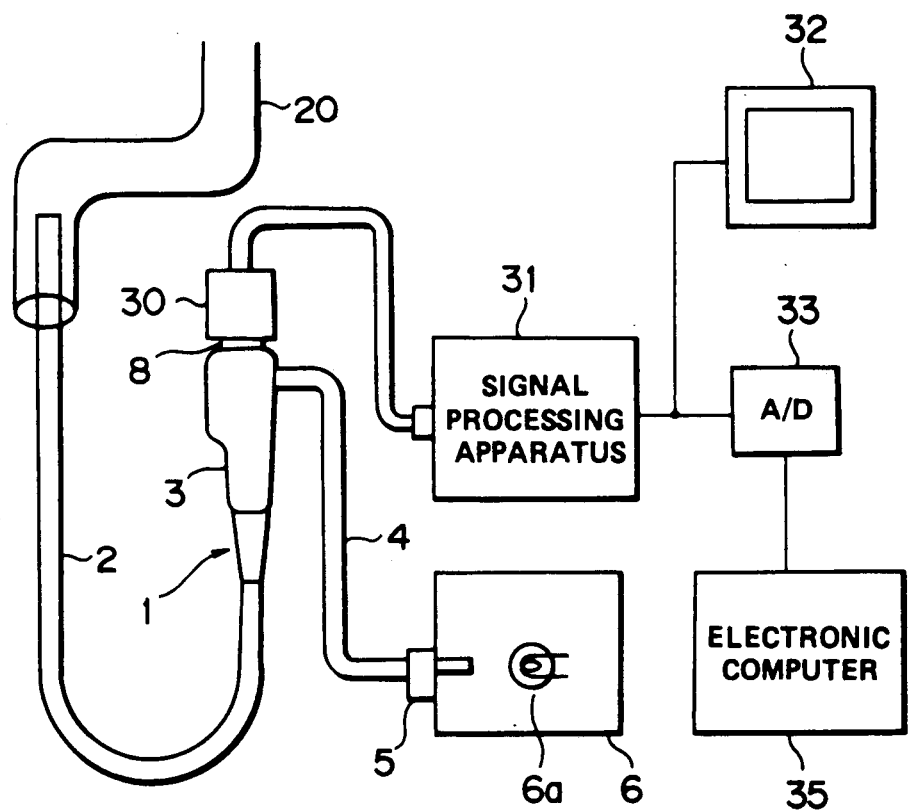
Figure 8:
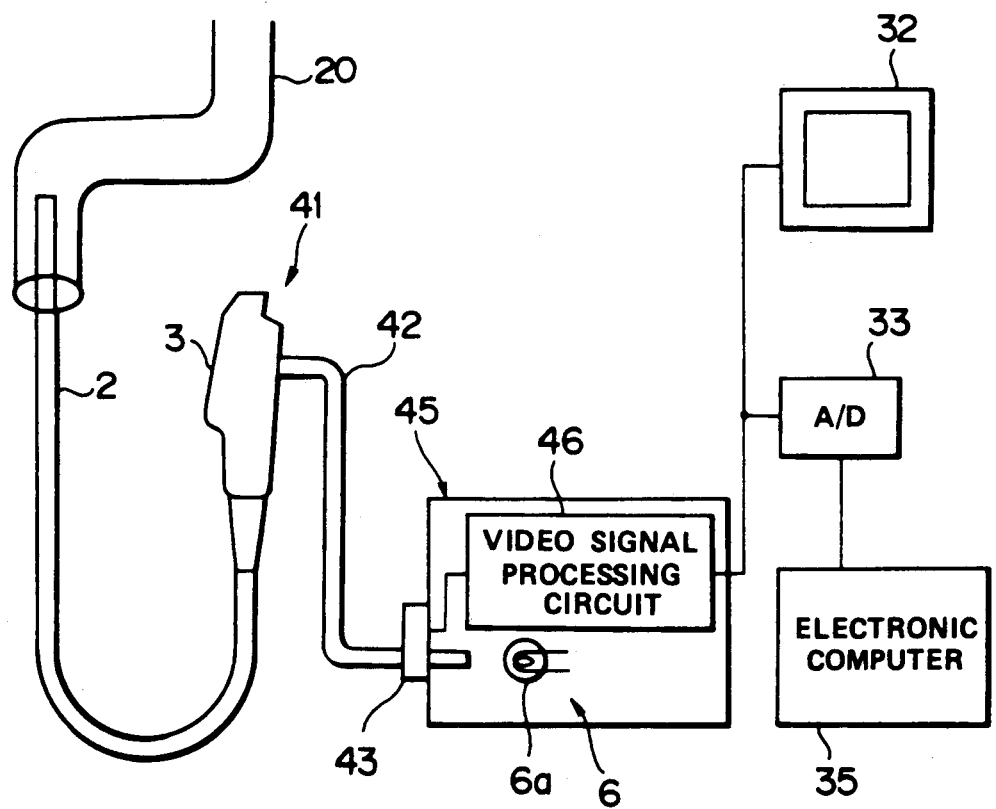

The method of detecting the insertion direction of an endoscope of this embodiment is applied to an endoscope apparatus shown, for example, in FIG. 7 or 8.

The endoscope apparatus shown in FIG. 7 is provided with a fiberscope 1 fed with illuminating light by a light source apparatus 6 and an externally fitted television camera 30 fitted to an eyepiece part 8. The formation of the above mentioned fiberscope 1 is the same as is shown in FIG. 1 and will not be explained here. The above mentioned externally fitted television camera 30 is provided, for example, with an image forming lens (not illustrated) forming an image of a light from the eyepiece part 8 and a solid state imaging device (not illuminated) arranged in the image forming position of this image forming lens. This externally fitted television camera 30 drives the above mentioned solid state imaging device and can be connected to a signal processing apparatus 31 which processes the output signal of this solid state imaging device. The video signal output from the signal processing apparatus 31 enters a monitor 32 and is converted to a digital form by an A/D converter 33. After conversion, this video signal enters an electronic computer 35 and can be input Into a memory (not illustrated) within this electronic computer 35. The endoscope image is displayed on the monitor 32. The method of detecting the insertion direction of an endoscope in this embodiment is carried out by the above mentioned electronic computer 35.

The endoscope apparatus shown in FIG. 8 is provided with a videoscope 41 instead of the fiberscope 1 and externally fitted television camera 30. The same as in the above mentioned fiberscope 1, this videoscope 41 is provided with an elongated flexible insertion sheath 2 and an operating part 3 connected to the rear end of this insertion sheath 2. A flexible universal cord 42 is extended sidewise from the operating part 3 and is provided at its tip with a connector 43 which can be connected to a control apparatus 45 containing a light source apparatus s and video signal processing circuit 46. A solid state imaging device (not illustrated) is arranged in the image forming position of the objective lens at the tip of the insertion sheath 2 of the videoscope 41. This solid state imaging device is connected to a video signal processing circuit 46 within the control apparatus 45 by way of the signal lines inserted through the insertion sheath 2, operating part and universal cord 42, and the connector 43. Also, the illuminating optical system of the above mentioned videoscope 41 is the same as the fiberscope 1. The illuminating light emitted by the lamp 6a of the light source apparatus 6 within the control apparatus 45 will enter the incident end of the light guide. The above mentioned solid state imaging device is driven by the video signal processing circuit 46 and the output signal of this solid state imaging device will be processed by the video signal processing circuit 46. The same as in the endoscope apparatus using the fiberscope 1, the video signal output from this video signal processing circuit 46 enters the monitor 32 and is converted to be in a digital form by the A/D converter 33. After conversion, the video signal enters the electronic computer 35 and will be stored into the memory (not illustrated) within this electronic computer 35. An endoscope image is displayed on the monitor 32. The method of detecting the insertion direction of an endoscope in this embodiment is carried out by the above mentioned electronic computer 35.

The method of detecting the insertion direction of an endoscope in this embodiment will be explained as follows.

Figure 9:
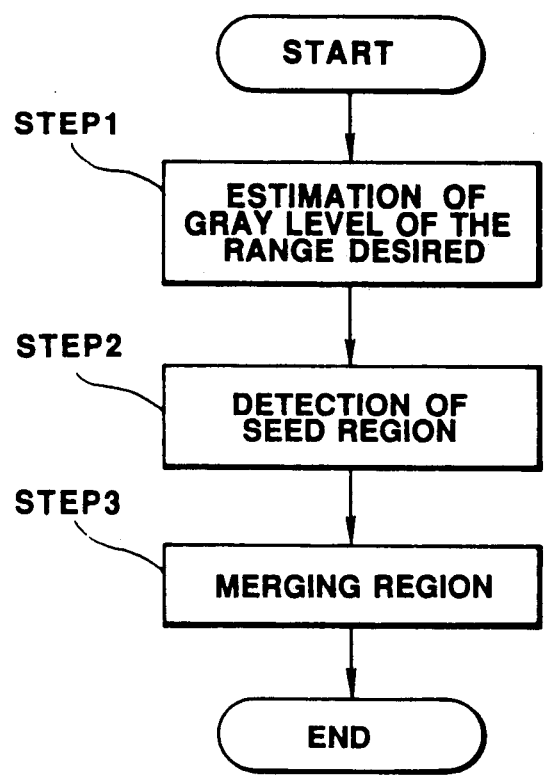

As shown in FIG. 9, the method of detecting the insertion direction of an endoscope in this embodiment comprises a step 1 of estimating a gray level of a desired range from an endoscope image stored into the electronic computer 35, a step 2 of detecting a seed region (i.e., a dark and uniform region) which becomes the insertion direction of an endoscope by using the gray level obtained by the above mentioned step 1 and a step 3 of merging neighboring areas of the seed region detected by the above mentioned step 2 and the seed region.

The above mentioned step 1 will be explained with reference to FIG. 10.

Figure 10:
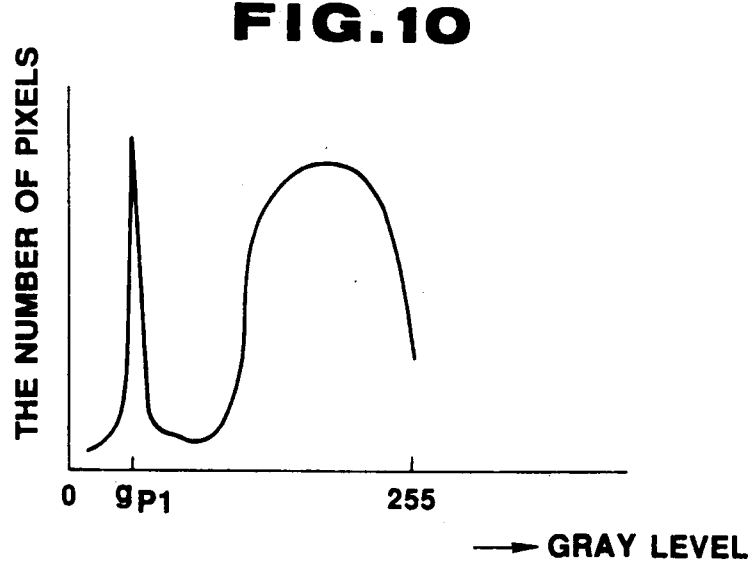

When a histogram with respect to the gray level on an endoscope image is constructed, the distribution as shown in FIG. 10 is displayed in many endoscope images. The first peak in the histogram, that is to say, the first peak from a dark side proves to correspond to the dark region in which an endoscope sheath should be inserted. Also, in the examples shown in FIG. 10, the gradation of the gray level is assigned 256. Then, in step 1, in order to estimate the required gray level range, the histogram with respect to the gray level is constructed and the gray level of the first peak is obtained. Then, in case the obtained gray level is $g_{p1}$ and the gradation of the gray level is 256, the required range of the gray level is provided with $g_{p1} \pm 5$. Thus, it is appropriate that the range of the required gray level has a difference of not much exceeding $\pm 5$; however, the difference is not limited to $\pm 5$.

Next, step 2 will be explained with reference to FIGS. 11 to 14.

Step 2 is roughly divided into the following two operations.

Operations (2-a): a pyramid of picture images based on a quadtree is constructed and the variance of each node and an average gray level are obtained.

Operations (2-b): a seed region is extracted by using a u-link.

Also, operations (2-a) are carried out in parallel with operations (2-b) in the operations of constructing the pyramid.

First, the operations (2-a) will be explained with reference to FIGS. 11 and 12.

The pyramid of picture images is a system of images obtained by gradually reducing the resolution of an picture image. In the pyramid of picture images based on the quadtree, four child nodes of a plane correspond to a parent node of the plane of an upper level.

The pyramid based on the quadtree is constructed by gradually forming picture images having $\frac{1}{4}$ resolution started from a pixel level of the original picture image.

Figure 11:
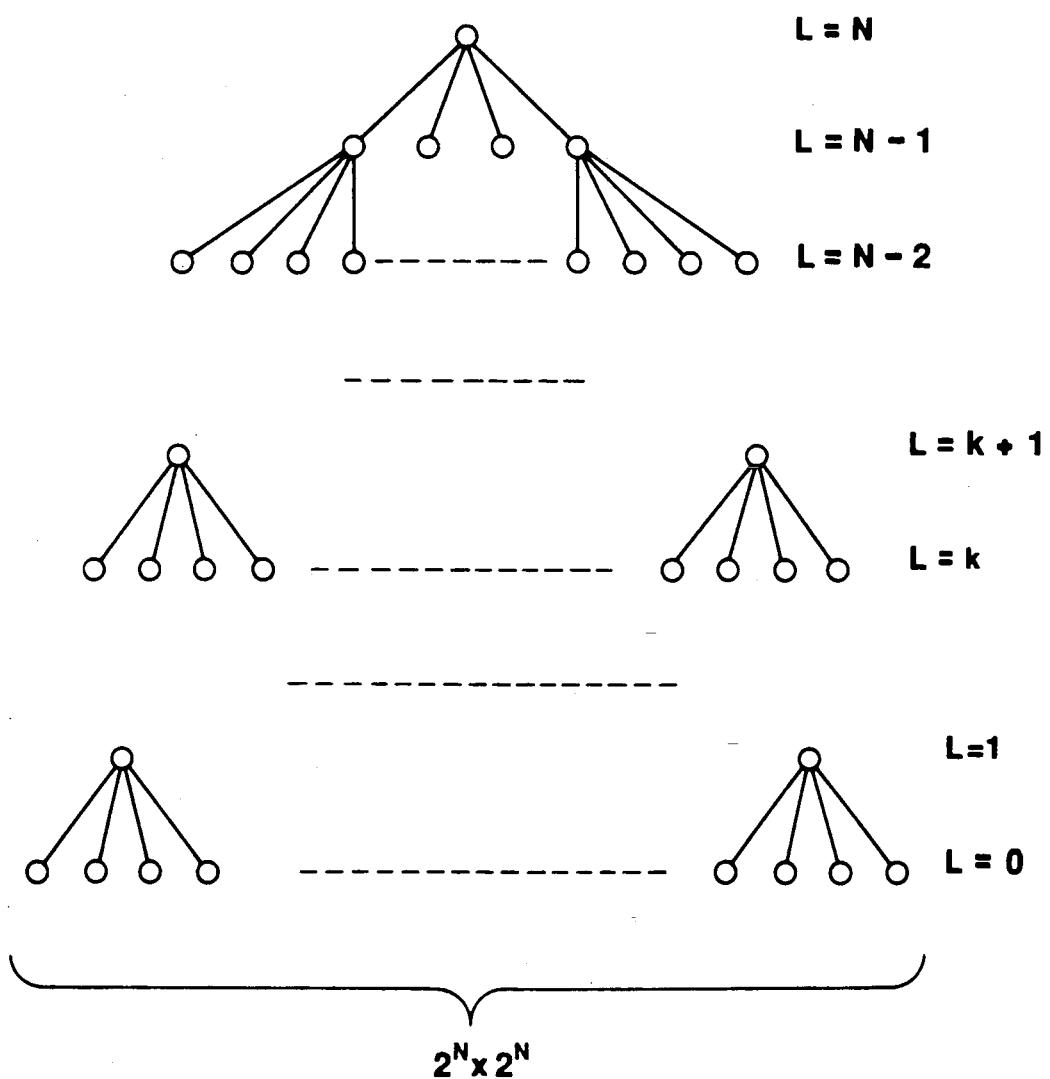
Figure 12:
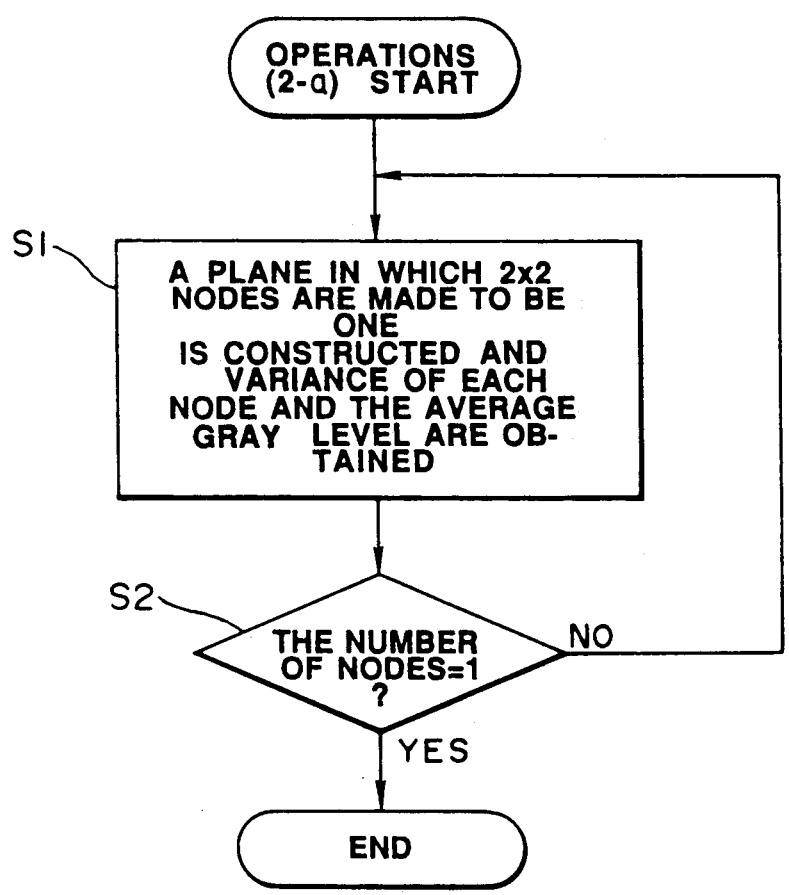

For example, as shown in FIG. 11, in case the total pixels of the original picture image number $2^N \times 2^N$, first of all, in step S1 in FIG. 12, a plane made of $2^{N-1} \times 2^{N-1}$ nodes, in which each region of $2 \times 2$ pixels is made to be a node, will be constructed.

Next, in step S2, a determination is made whether the number of nodes is one or not. In case of NO, the process goes back to S1 and a plane made of $2^{N-2} \times 2^{N-2}$ nodes, in which each $2 \times 2$ node in the above mentioned plane is made to be a node, will be constructed. In case of YES, the operations (2-a) will end. That is, the operations of the above mentioned step S1 will be continued until the number of nodes becomes one.

As shown in FIG. 11, in the case where the total pixels of the original picture image number $2^N \times 2^N$, the pyramid based on the quadtree is made of (N+1) planes and the level L of the plane having $2^n \times 2^n$ nodes will be provided by the next computation:

$$L = N - n$$

In this embodiment, as shown in step S1 in FIG. 12, when a pyramid is constructed, the average gray level of a parent node and variance of the gray level are calculated using the average gray level and variance of the gray level of four child nodes.

Here, if variances of four nodes at a level k are $V_{k1}$, $V_{k2}$, $V_{k3}$ and $V_{k4}$ and their average gray levels are $\mu_{k1}$, $\mu_{k2}$, $\mu_{k3}$ and $\mu_{k4}$, $V_{k+1}$ which is the variance of the parent node and has the above mentioned four nodes of its child will be calculated using the following computation:

$$V_{k+1} = \tfrac{1}{4}[V_{k1} + V_{k2} + V_{k3} + V_{k4} + \mu_{k1}^2 + \mu_{k2}^2 + \mu_{k3}^2 + \mu_{k4}^2] - [\tfrac{1}{4}(\mu_{k1} + \mu_{k2} + \mu_{k3} + \mu_{k4})]^2 \quad (1)$$

Similarly, the average gray level is calculated using the following computation:

$$\mu_{k+1} = \tfrac{1}{4}[\mu_{k1} + \mu_{k2} + \mu_{k3} + \mu_{k4}] \quad (2)$$

Accordingly, computation (1) can be also calculated as follows:

$$V_{k+1} = \tfrac{1}{4}[V_{k1} + V_{k2} + V_{k3} + V_{k4} + \mu_{k1}^2 + \mu_{k2}^2 + \mu_{k3}^2 + \mu_{k4}^2] - \mu_{k+1}^2 \quad (3)$$

That is to say, the variance $V_{k+1}$ and the average gray level $\mu_{k+1}$ of the node at a level (k+1), can be calculated using the variances $V_{k1}$, $V_{k2}$, $V_{k3}$ and $V_{k4}$ of four child nodes of the node and their average gray levels $\mu_{k1}$, $\mu_{k2}$, $\mu_{k3}$ and $\mu_{k4}$.

Also, in case of a level 0(zero), its variance becomes 0(zero) and its average gray level is the gray level of each pixel itself.

As mentioned above, in operations (2-a), a pyramid based on the quadtree will be constructed starting from the bottom level (level L=0) up to the root level (level L=N) and variance of each node and its average gray level will be calculated.

Figure 13:
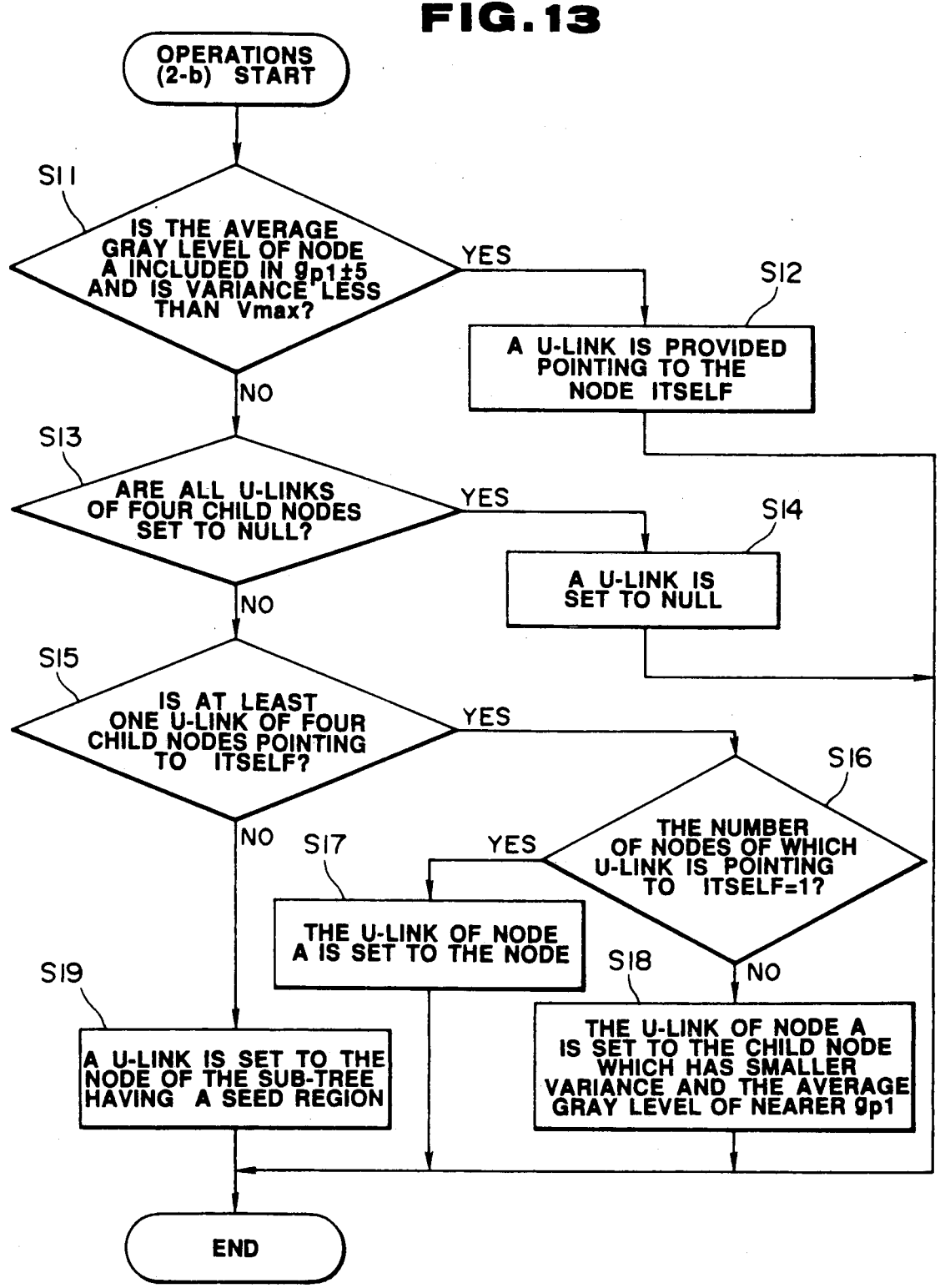

Next, operations (2-b) will be explained with reference to FIGS. 13 and 14.

During the process of the above mentioned operations (2-a), it is examined whether the average gray level of each node is included in the provided range at step 1 or not, and whether variance is $V_{max}$ and less than a threshold which was previously set and a dark and uniform region is detected.

In this embodiment, in order to indicate a dark and uniform seed region, a u-link (a special pointer belongs to each node) is introduced. This u-link is provided with the following rules.

Rule 1: Where the average gray level and variance of a node satisfy the above mentioned conditions, a u-link is provided in the form of a pointer to the node itself. Then, its node is designated as the seed region.

In case the average gray level and variance of a node does not satisfy the above mentioned conditions, the following rules 2 and 3 are applied.

Rule 2: The four child nodes of the node are examined and the node having the spatially largest seed region is selected. Then, a u-link directed from the parent node to the above mentioned child nodes is provided and the seed region of the child node is taken as the seed region of a parent node. Also, in the case where the seeds supplied by several child nodes are the same size, a child node having a seed with a smaller variance and an average gray level which is closer to the gray level provided in step 1 will be selected.

Rule 3: In the case where none of the four child nodes of the node have seed regions in their sub-trees, a u-link points to nothing (points to NULL).

Figure 14:
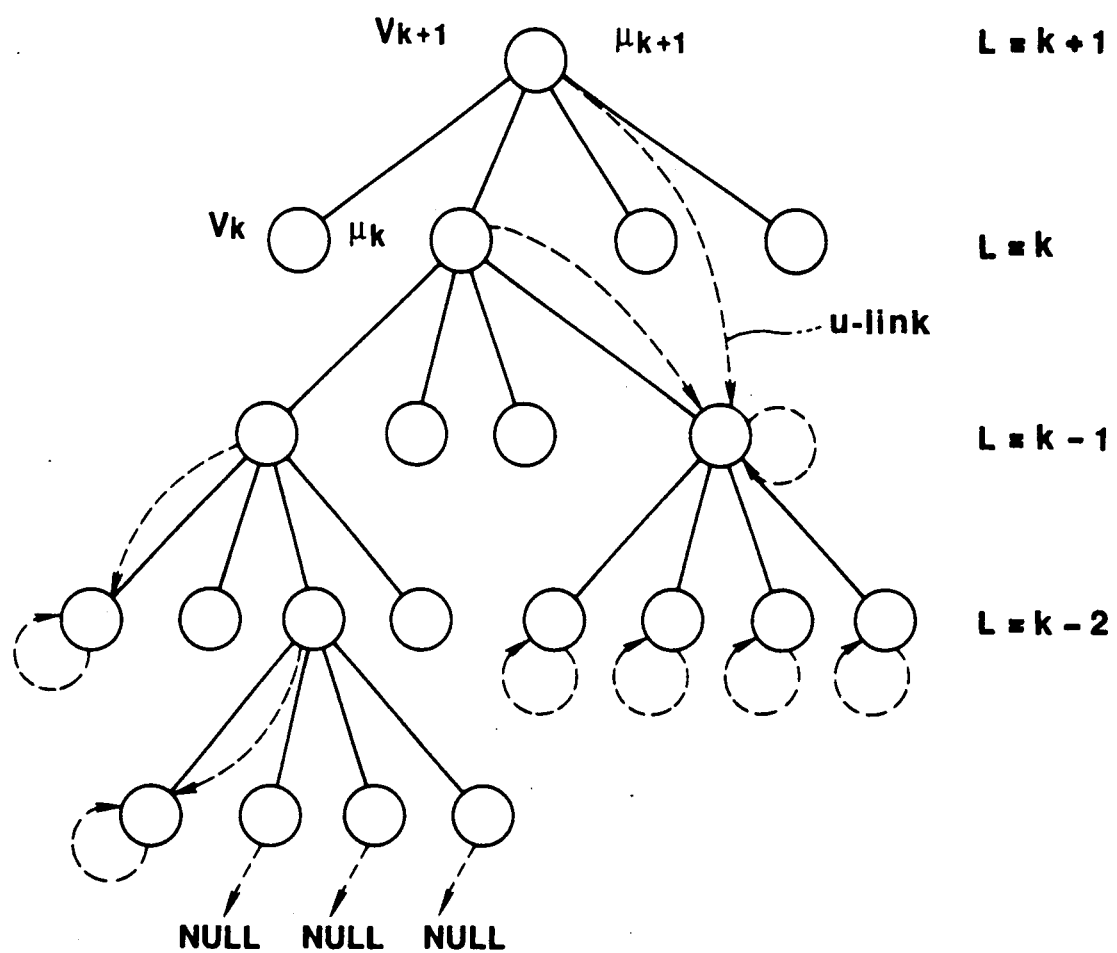

An example of u-link provided according to the above mentioned rules is shown in FIG. 14. Also, in this figure, broken lines represent u-links.

The operations (2-b) will be explained using a flow chart of FIG. 13.

First, in step S11, a determination is made whether an average gray level of a node (node A, for example) is included in $g_{p1} \pm 5$ and its variance is $V_{max}$ and less. In case of YES, in step S12, a u-link is provided in the form of a pointer to the node itself and will end.

In case of NO, in step S13, a determination is made whether all u-links of four child nodes are set to NULL or not. In case of YES, in step S14, a u-link is set to NULL and will end.

In case of NO, in step S15, a determination is made whether at least one u-link of four child nodes is pointing to itself or not. In case of YES, in step S16, a determination is made whether the number of nodes of which u-link is recurring to itself is one or not. In case of YES, in step S17, the u-link of node A is set to the node and will end. In case of NO in step S16, the u-link of node A is set to the child node which has a smaller variance and an average gray level closer to $g_{p1}$ in step 18, and will end.

In case of NO in the above mentioned step S15, a u-link is set to the node of the sub-tree having the largest seed region in step 19 and will end.

As stated above, these operations (2-b) are carried out in parallel with the pyramid architecture of the operations (2-a). Therefore, when the pyramid is completed, the u-link of the root node of the pyramid will point to a square region which is the spatially largest and extremely uniform in the total picture image and also is close on the gray level estimated in step 1. That is to say, the region of the node to which the u-link of the root node points should be the insertion direction of an endoscope that is being required.

Next, step 3 will be explained.

Operations may be completed in step 2; however, in the case where more accurate operations are required, neighboring areas of the seed region obtained in step 2 will be merged with the seed region. In this case, when the following conditions are satisfied, neighboring areas are merged.

Condition 1: An average gray level is included within the gray level range estimated in step 1.

Condition 2: variance is less than the value which is previously set.

Also, in the above mentioned merging, if a node of a plane which is lower than the seed region obtained in step 2 is used in the pyramid, it is possible to extract the region more accurately.

Thus, according to this embodiment, since a dark region is extracted while brightness and variance are being examined together, a region which is dark and has brightness uniformity can be extracted without performing back tracking and the insertion direction of an endoscope can be detected in a short processing time.

The insertion direction of an endoscope can be accurately detected by examining variances, except for regions with irregular brightness.

Furthermore, the range of appropriate gray levels adapted to an endoscope image can be provided by setting the gray level range indicating the insertion direction based on the histogram with respect to the gray level of the original picture image.

Furthermore, when variance and the average gray level are included within a set value and the spatially largest region is extracted, the processing time can be reduced by introducing the u-link.

In the insertion direction of an endoscope detected by the method of the present invention, the endoscope may be inserted manually by the curving operation and advancing insertion operation by the endoscope operator, or the endoscope may be inserted by automatically directing the tip in the detected insertion direction by the apparatus.

In this invention, it is apparent that embodiments different in a wide range can be formed on the basis of this invention without departing from the spirit and scope of the invention. This invention is not restricted by its specific embodiments except being limited by the attached claims.

What is claimed is:

1. A method of detecting the direction of insertion of an endoscope comprising the steps of:

forming a system of images including a plurality of picture images from an endoscope image, said picture images having a different number of picture image areas from the endoscope image;

extracting a largest uniform gray level region, including an average gray level and smallest variance of gray level within predetermined ranges, by examining the average gray level and variance of the gray level of respective picture image areas in said plurality of picture images formed by said forming step, said forming step and said extracting step are carried out in parallel, said extracting step includes using a u-link when said region is extracted, said u-link pertaining to a specific picture image area points to the specific picture image area itself where the average gray level and variance of the gray level of the specific picture image area are included within the predetermined ranges, where the average gray level and variance of the gray level of the specific picture image areas are not included within the predetermined ranges, said u-link pertaining to a specific picture image area points to a largest picture image area in which the average gray level and variance of the gray level of the specific picture image area are included within the predetermined ranges among respective picture image areas corresponding to said specific picture image area in a picture image at a lower plane of the system of images rather than a picture image to which said specific picture image area belongs; and utilizing the region extracted by said extracting step as an endoscope insertion direction.

2. A method according to claim 1 wherein said forming step includes gradually forming picture images of less picture image areas while reducing the number of picture image areas to ¼, so that, where the number of picture image areas is reduced to ¼, the average gray level and variance of the gray level of one picture image area in a picture image of less picture image areas are obtained based on the average gray level and variance of the gray level of 2×2 child picture image areas corresponding to one picture image area in a picture image of more picture image areas.

3. A method according to claim 1, further comprising a step of obtaining an average gray level range provided in order to extract the region in said extracting step based on a histogram with respect to the gray level of the original endoscope image.

4. A method according to claim 3 wherein said obtaining step includes obtaining said range based on a gray level corresponding to a first peak from a dark side in said histogram.

5. A method according to claim 1 wherein said u-link points to a picture image area at the lower plane in which the variance is smaller and the average gray level is nearer a predetermined value within said predetermined ranges, where a plurality of the largest picture image areas at the lower plane in which the average gray level and variance of the gray level are included within the predetermined ranges exist among respective picture image areas at the lower plane corresponding to said specific picture image area in the picture image at the lower plane of the system of images rather than the picture image to which said specific picture image area belongs.

6. A method according to claims 1 wherein said extracting step makes the picture image area pointed to by the u-link of a root in the system of images in a region to be extracted.

7. A method according to claim 1, further comprising a step of merging said region extracted by said extracting step and neighboring areas of said extracted region in which the average gray level and variance of the gray level are included in the predetermined ranges.

8. A method according to claim 7 wherein said merging step includes merging picture image areas at a further lower plane in a picture image at the lower plane of the system of images rather than the picture image to which the region extracted by said extracting step belongs.

9. A method according to claim 1 wherein said endoscope image is obtained by a television camera fitted to an eyepiece part of an endoscope wherein naked-eye observation is possible.

10. A method according to claim 1 wherein said endoscope image is obtained by an imaging means provided in the endoscope.

* * * * *